United States Patent [19]

Kajiura et al.

[11] 4,319,269
[45] Mar. 9, 1982

[54] EXTERNAL APPEARANCE INSPECTING SYSTEM

[75] Inventors: Toshihiro Kajiura, Osaka; Norio Oita, Kobe; Masahiro Mori, Osaka; Yuichi Fukui, Settsu, all of Japan

[73] Assignee: Kanebo Limited, Tokyo, Japan

[21] Appl. No.: 71,354

[22] Filed: Aug. 30, 1979

[30] Foreign Application Priority Data

Nov. 24, 1978 [JP] Japan .............................. 53-145728

[51] Int. Cl.³ .............................................. H04N 7/18
[52] U.S. Cl. ...................................... 358/106; 358/126
[58] Field of Search ................... 358/93, 101, 106, 126

[56] References Cited

U.S. PATENT DOCUMENTS

| | | | |
|---|---|---|---|
| 2,798,603 | 7/1957 | Richards | 358/106 |
| 3,598,907 | 8/1971 | Drinkuth | 358/106 |
| 3,775,556 | 11/1973 | Nagamatsu | 358/106 |
| 4,163,991 | 8/1979 | Burrig | 358/106 |

Primary Examiner—Joseph A. Orsino, Jr.
Attorney, Agent, or Firm—Abelman, Frayne & Rezac

[57] ABSTRACT

An external appearance inspecting system is disclosed. In the system, a TV camera is employed for forming a TV image scope. A detection area and an inspection area are electrically created in the TV image scope. The appearance of an image of an object to be inspected is detected by the detection area. Then, the image of the object is inspected by the inspection area. The inspection area is created at the $(N+K)_{th}$ ($N=1, 2, 3 \ldots$, $K=1, 2, 3 \ldots$) scanning field of the TV image scope, if the image of the object is detected by the detection area which was created at the $N_{th}$ scanning field.

9 Claims, 27 Drawing Figures

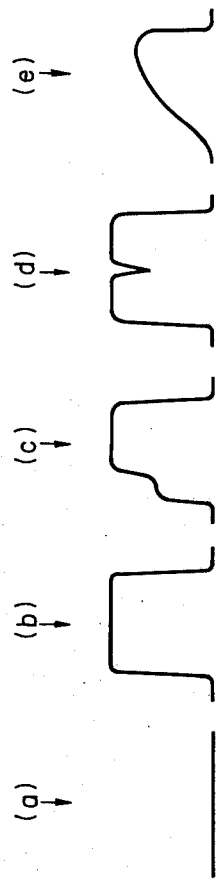
Fig. 5A
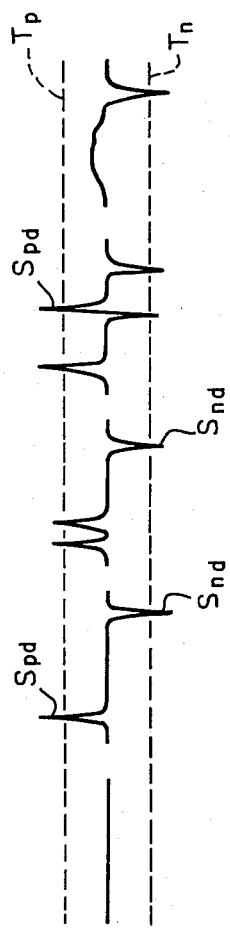
Fig. 5B
Fig. 5C
| | | | | | |
|---|---|---|---|---|---|
| POS | 0 | — | 2 | 2 | 0 |
| NEG | 0 | — | 1 | 2 | — |
| DEC | ○ | ○ | × | × | × |

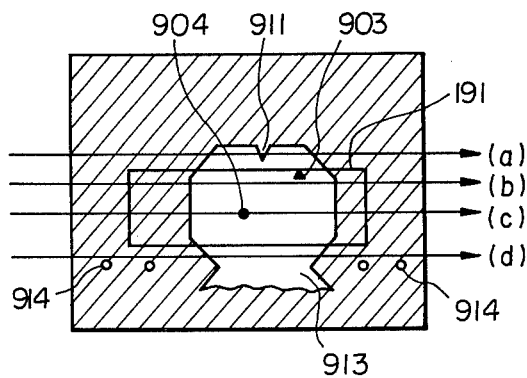
Fig. 13
Fig. 14A
Fig. 14B
Fig. 14C
Fig. 14D
Fig. 14E
Fig. 14F
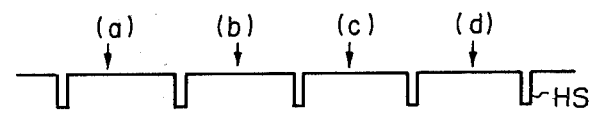
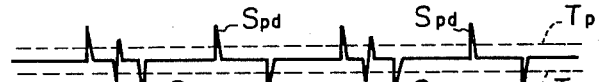
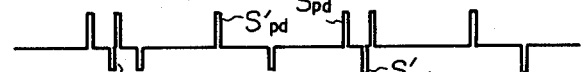
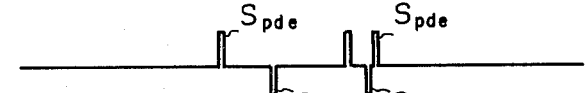

EXTERNAL APPEARANCE INSPECTING SYSTEM

The present invention relates to an external appearance inspecting system.

The external appearance inspecting system may be introduced in a factory for producing, through a mass production process, something having the same external appearance on which an external appearance inspection has to be made. In the present invention, the external appearance inspecting system is described by taking, for example, a system in which mass produced tablets are arranged in a single line on a conveyor so that each tablet may be inspected individually.

Since the tablets are inserted into human bodies, each tablet must be produced under the utmost sanitary conditions. Accordingly, none of the mass produced tablets should contain visible defects on the external surface thereof. Visible defects are, for example, blots, adhesion of alien substances to the tablet, scratches and so on. Therefore, it is necessary to give an external appearance inspection to all mass produced tablets before they are delivered to be used in humans.

In the external appearance inspecting system of the prior art, the inspection of the external appearance of each tablet is achieved by means of the human eyes of the inspectors. Therefore, the criteria for determining whether or not the inspected tablets is good varies, due to a difference between personal inspecting abilities, if the tablets are inspected by a plurality of inspectors. The personal inspecting abilities may be defined as the eyesight, expertness and strictness of each inspector. Further, generally, the inspector completes the inspection at a speed per second of two or three tablets, at the most. Consequently, within the process for producing tablets, the inspection process becomes one of the processes which requires a large time for completion and also necessitates many workers, that is inspectors.

The latest tendency is to employ a TV camera in the external appearance inspecting system, in order to eliminate the aforementioned inconveniences created in the system of the prior art. Thereby, the human eye inspection of the prior art is substituted by the TV camera. However, in a known inspecting system being provided with the TV camera, it is very difficult to inspect tablets, with a high degree of accuracy, which are being moved rapidly and continuously on a conveyer on which the mass produced tablets are arranged serially in a line, due to the following two short comings. Firstly, in the known TV inspecting system, it is necessary to employ a means for sampling a single scanning field of a TV signal, such as an inspection scanning field, which field must contain video signals representing each tablet. This sampling means is usually comprised of a photosensor being located at a position preceding the flow of tablets to be inspected, and the photosensor detects the appearance of the tablet to be inspected. The sampling means is also comprised of a delay circuit which receives delay circuit which receives the output from the photosensor. The delay circuit produces a signal which indicates a predetermined delay time from the time when the photosensor initially detects the appearance of the tablet, so as to determine the time when the tablet will be completely stopped within the scope of the TV camera, by taking into account the transferring speed of the conveyer and the distance between the photosensor and the scope of the TV camera. However, the photosensor cannot correctly detect some tablet which has a spherical shape and brilliance, such as if the tablet is sugar coated. Further, the delay circuit cannot produce a signal which indicates a correct delay time when an undesirable slight position change of the tablet occurs during the time the tablet is moved from said photosensor area to the TV camera, area said position change due to, for example, a vibration generated in the conveyor on which the tablets are mounted. Thus, the known inspecting system cannot operate with a high degree of accuracy and a high processing speed. Secondly, in the known inspecting system, there is no best means for discriminating an image indicating a correct pattern of the tablet from an image indicating an incorrect or pseudo pattern of the tablet. The pseudo pattern is created by, for example, dust scattered around the tablet and light reflected from the edge portions of the tablet. The discrimination between the above mentioned correct and pseudo patterns of the tablet is performed, in the known inspecting system, by utilizing an electric inspection window in the scope of the TV camera. The inspection window is effective for determining the image representing only the correct pattern of the tablet. However, if the correct pattern of the tablet is shifted outside the limits of the inspection window, due to the vibration of the conveyor, the desired function of the inspection window is lost. Thus, the known inspecting system cannot operate with a high degree of accuracy.

Therefore, it is an object of the present invention to provide an external appearance inspecting system which can make it easy to inspect objects having the same external appearance with a high degree of accuracy and a high processing speed, when compared to the above mentioned known inspecting system being provided with a TV camera.

The present invention will be more apparent from the ensuing description, with reference to the accompanying drawings wherein:

FIG. 5A shows typical waveforms of video signals;

FIG. 5B shows waveforms of positive and negative decision signals $S_{pd}$ and $S_{nd}$;

FIG. 5C shows a table used for explaining the meaning of the waveforms shown in FIGS. 5A and 5B;

FIG. 13 is a plan view of a TV image scope, used for explaining the operation of the external appearance inspecting system shown in FIG. 10, and;

FIGS. 14A through 14F depict timing charts of signals, used for explaining the operation of the external appearance inspecting system shown in FIG. 10, with reference to FIG. 13.

Figure 1:
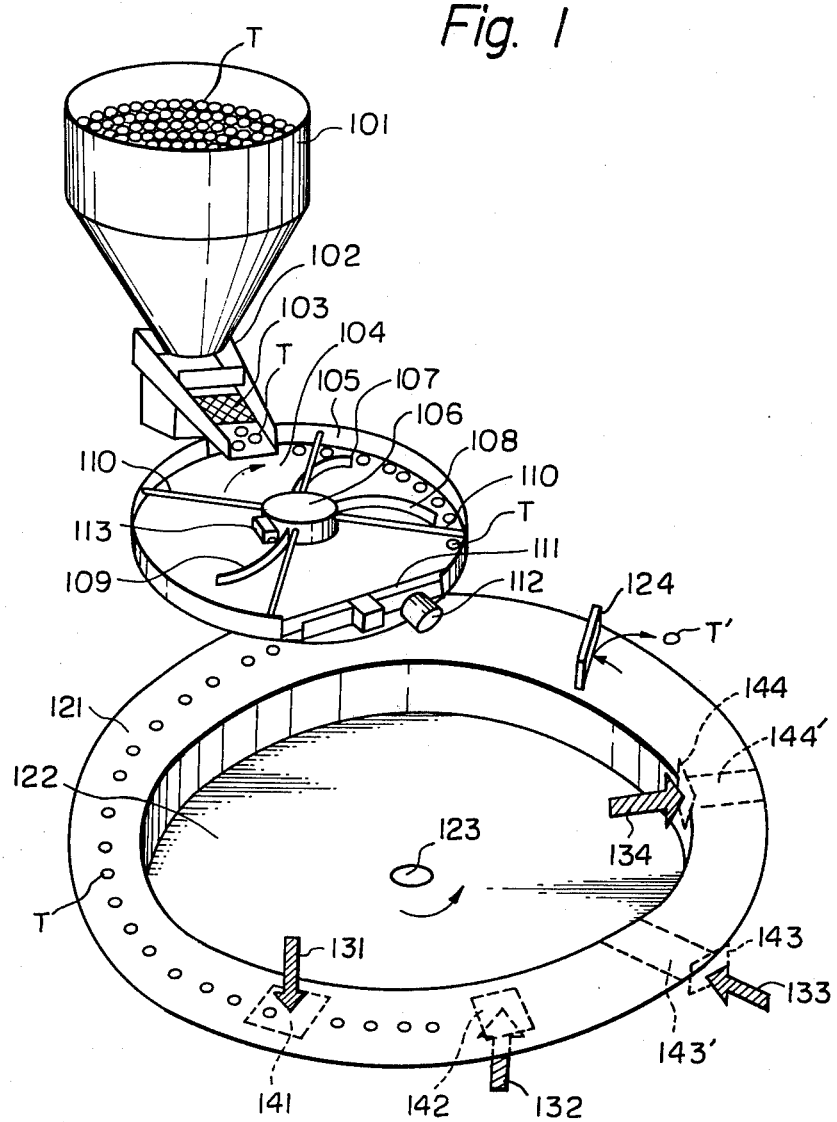
FIG. 1 is a general view of an apparatus for feeding objects to be inspected, by which apparatus an external appearance inspecting system of the present invention can be made efficiently and with a high degree of accuracy.

In FIG. 1, which is a general view of an apparatus for feeding objects to be inspected, by which apparatus an external appearance inspecting system of the present invention can be operated efficiently and with a high degree of accuracy, the reference numeral 101 represents a hopper which holds a great number of mass produced objects having the same external appearance, for example tablets, to be inspected. The tablets T are supplied onto a rotating table 104 by way of a vibrating conveyer 102 having a net 103 therein. The table 104 rotates in a clockwise direction around a fixed shaft 106. The shaft 106 fixedly holds three commutating guides 107, 108 and 109. The shaft 106 also fixedly supports a circular fence 105 via four bars 110. The fence 105 has a selection gate 111 of a certain width and a certain height. The tablets, which are allowed to pass through the selection gate 111, under the vibration of a vibrator 112, onto a ring-shape conveyor 121 which is made of transparent glass. A photosensor 113 detects the volume of tablets which have not been allowed to pass through the gate 111, so as to control the feeding speed. The glass conveyer 121 forms a turn table together with a cap 122, as one body. Thus, the turn table forms a hat-like shape and rotates in a counter-clockwise direction by means of a rotating shaft 123. The tablets T which are conveyed close to the gate 111, are spread out by means of a guide 124 (see tablet T').

In FIG. 1, the hatching arrows 131 through 134 specifically denote each view direction of the TV camera (explained hereinafter). The dotted areas 141, 142, (143, 143') and (144, 144') specifically denote the scope of each TV camera. All the scopes may be active at the same time, or one or two of the scopes are selected in accordance with the purpose of the inspection. The tablets are provided for inspection when each tablet is traversed across the scope 141, 142, (143, 143') or (144, 144'). If any tablet fails the inspection, this tablet is snapped away by actuating a snapping device. Since the snapping device is not important in the present invention and also is a publicly known device, the snapping device is not described in detail. The feed apparatus shown in this FIG. 1 is very useful for feeding tablets serially one by one along a line with a very small constant space between each two adjacent tablets, and also the transparent glass conveyer 121 is very useful for achieving the inspection by means of the TV camera.

Figure 2:
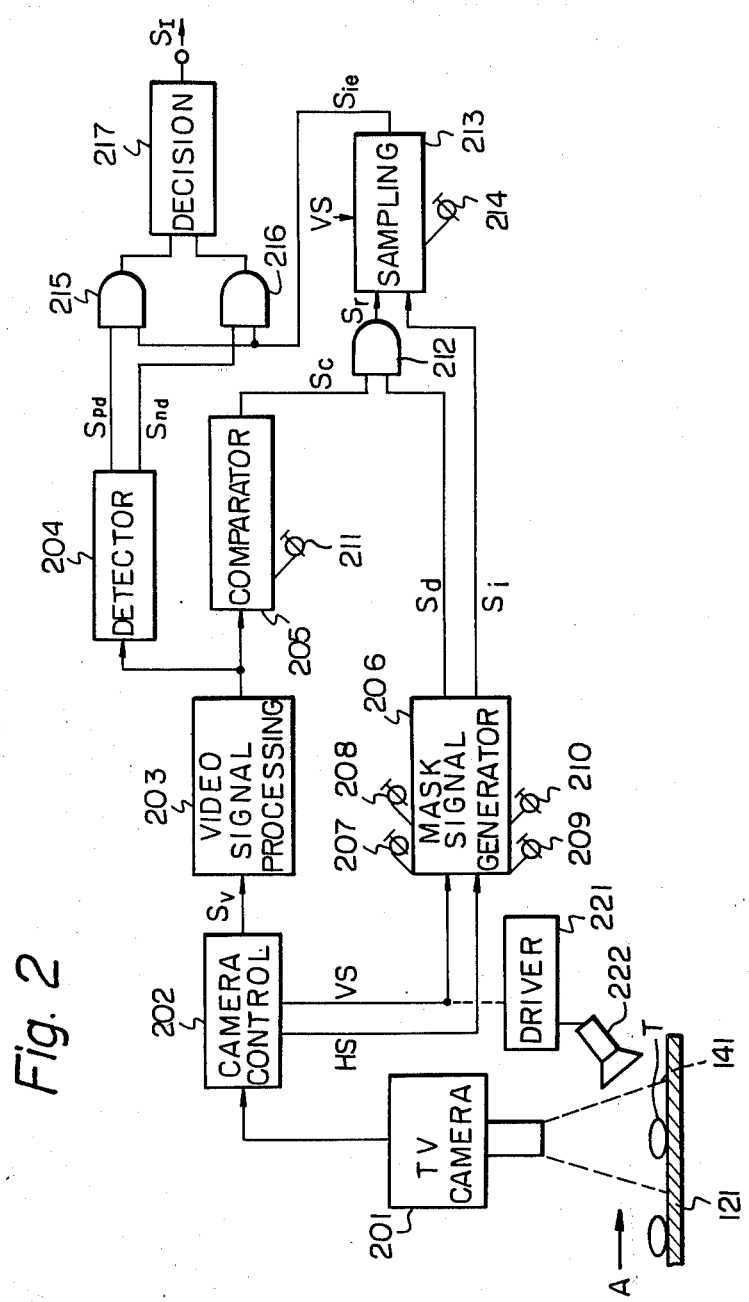
FIG. 2 is a block diagram of a first embodiment of an external appearance inspecting system according to the present invention.

In FIG. 2, which is a block diagram of a first embodiment of the external appearance inspecting system according to the present invention, the tablets are transferred, in the direction of arrow A, one by one, by means of the glass conveyer 121. When the tablet T is traversed across the scope 141, the external appearance thereof is transformed into a corresponding video signal by means of a TV camera 201. The video signal $S_v$, together with the horizontal synchronizing signal HS and the vertical synchronizing signal VS thereof, is produced from a conventional camera control unit 202. A video signal processing circuit 203 receives the video signal $S_v$ from the unit 202 and processes the received video signal $S_v$ so as to eliminate undesired noise components therefrom and amplify the signal $S_v$. Then the processed video signal is sent from the circuit 203 to both an appearance detector 204 and a level comparator 205.

On the other hand, the horizontal and vertical synchronizing signals HS and VS are sent to an areal mask signal generator 206. The generator 206 produces both a detection area signal $S_d$ and an inspection area signal $S_i$ (the detection and inspection areas will be explained in detail hereinafter). The detection area signal $S_d$ acts as an area signal for creating the detection area in the TV image scope, which detection area is provided so as to initially detect the image of the appearance of the tablet in the TV image scope. The inspection area signal $S_i$ acts as an area signal for creating the inspection area in the TV image scope, which inspection area is provided so as to inspect the image of the entire external appearance of the tablet. The generator 206 is provided with adjusters 207 and 208 which adjust the position and the size of the detection area created in the TV image scope and adjusters 209 and 210 which adjust the position and the size of the inspection area created in the TV image scope.

The level comparator 205 is provided with an adjuster 211. The threshold of the level comparison can be adjusted by the adjuster 211, so that the image of the tablet is clearly separated from the image of the background in the TV image scope. Thus, the comparator 205 produces a signal $S_c$ which indicates that the image of at least a part of the tablet exists in the TV image scope. If the image of at least a part of the tablet is detected in the detection area, both signals $S_c$ and $S_d$ are supplied to an AND gate 212 simultaneously and, then the gate 212 produces a recognition signal $S_r$. The signal $S_r$ activates a sampling circuit 213 so as to sample a $(N+K)_{th}$ scanning field of the TV image scope, in a case where the signal $S_r$ was produced in a $N_{th}$ scanning field. The number K may be predetermined one of positive integers, such as one or two or three. The above mentioned predetermined number of scanning fields is adjustable by means of an adjuster 214. The inspection area signal $S_i$ is effective only in the sampled scanning field, by means of the circuit 213.

An effective inspection area signal $S_{ie}$, which is provided at time the sampled scanning field is activated, is applied to both AND gates 215 and 216 so as to open these gates. Then, a positive decision signal $S_{pd}$ and a negative decision signal $S_{nd}$ are supplied to a final decision circuit 217 via AND gates 215 and 216, respectively. The circuit 217 determines whether or not the tablet being inspected passes the inspection, and the circuit 217 produces a resultant inspection signal $S_I$ which has logic "1" if the tablet does not pass the inspection. The signal $S_I$ having logic "1" may be used for actuating the aforesaid snapping device, so that the tablet having a visible defect thereon is snapped away from the conveyor, or it can actuate an alarm.

Figure 3:
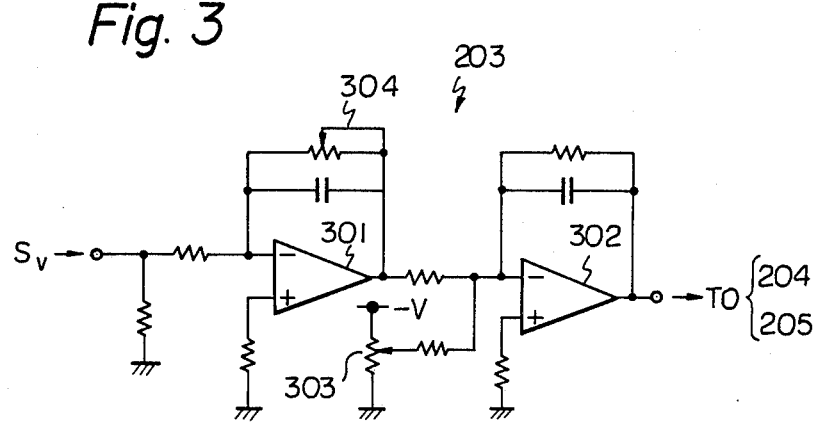
FIG. 3 is a circuit diagram showing an example of a video signal processing circuit 203 shown in FIG. 2.

In the system shown in FIG. 2, the video signal processing circuit 203 can be constructed in accordance with, for example, a circuit diagram shown in FIG. 3. As previously mentioned, the circuit 203 operates so as to amplify the video signal $S_v$ and also to eliminate the high frequency noise component contained in the signal $S_v$. In FIG. 3, the circuit 203 is comprised of operational amplifiers 301, 302, resistors, variable resistors and capacitors. The reference symbol "$-V$" denores a negative $d_c$ supply. The amplifiers 301 and 302, as one body, operate as a low-pass filter so that the above mentioned high frequency noise component can be eliminated from the video signal $S_v$. At the same time, the amplifiers 301 and 302, as one body, operate as an amplifier so that the video signal $S_v$ can be amplified. The variable resistor 303 may be controlled so as to adjust a zero clamp level, if necessary, and the variable resistor 304 may be controlled so as to obtain an optimum value of gain, if necessary.

Figure 4:
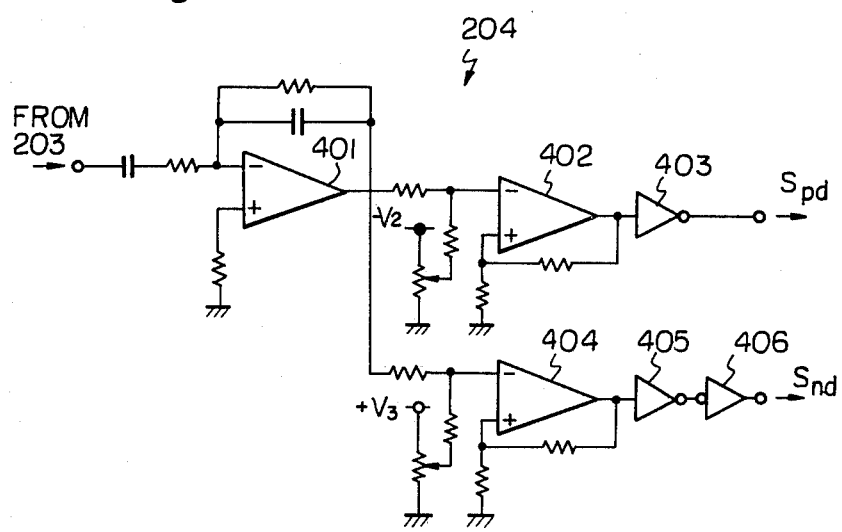
FIG. 4 is a circuit diagram showing an example of an appearance detector 204 shown in FIG. 2.

In the system shown in FIG. 2, the appearance detector 204 can be constructed in accordance with a circuit diagram shown in FIG. 4. The detector 204 detects visible features and also visible defects, such as blots, adhesion of alien substances, scratches and so on. In FIG. 4, the appearance detector 204 is comprised of operational amplifiers 401, 402, 404, inverters 403, 405, resistors, variable resistors and capacitors. The video signal supplied from the aforesaid circuit 203 is differentiated by a differentiating circuit being comprised of the amplifier 401. The differentiated video signal is applied to both a positive comparator, being comprised of the amplifier 402, and a negative comparator, being comprised of the amplifier 404, simultaneously. A suitable negative biassing voltage from a negative $d_c$ supply "$-V_2$" and a suitable positive biassing voltage from a positive $d_c$ supply "$+V_3$" are, respectively applied to the respective inverse input terminals of the amplifiers 402 and 404. Thus, a positive trigger pulse is produced, as the positive decision signal $S_{pd}$ (see FIG. 2), from the inverter 403. A negative trigger pulse is produced in response to the negative decision signal $S_{nd}$ (see FIG. 2) from the inverter 406 via the inverter 405. The positive and negative decision signals are clarified with reference to FIGS. 5A, 5B and 5C. FIG. 5A depicts typical patterns of waveforms of the video signal. FIG. 5B depicts waveforms of the positive and negative decision signals $S_{pd}$ and $S_{nd}$. FIG. 5C shows a table, used for explaining the meaning of the waveforms depicted in FIGS. 5A and 5B. In FIGS. 5A, 5B and 5C, column (a) represents a mode in which the video signal indicates the image of the background, column (b) represents a mode in which the video signal indicates the image of the tabloid having no visible defects thereon, column (c) represents a mode in which the video signal indicates the image of the tablet having some visible defect on the shoulder thereof, column (d) represents a mode in which the video signal indicates the image of a tablet having some visible defect on the top thereof and column (e) represents a mode in which the video signal indicates the image of a tablet having a scratch on the top thereof. In FIG. 5c, the top row (POS) shows the number of each signal $S_{pd}$, the peak amplitude of which is higher than a positive threshold level $T_p$ (see FIG. 5B), a middle row (NEG) shows the number of each signal $S_{nd}$, the peak amplitude of which is lower than a negative threshold level $T_n$ (see FIG. 5B), and a bottom row (DEC) shows decisions representing whether or not each video signal includes visible defects. In the bottom row (DEC) the symbol "O" represents no defect is found, while the symbol "X" represents some visible defect is found. These decisions are made by means of the final decision circuit 217. The circuit 217 includes a threshold level generator for producing the threshold levels $T_p$ and $T_n$ (see FIG. 5B) and a logic circuit which receives the signals $S_{pd}$ and $S_{nd}$, the peak levels of which exceed the respective threshold levels. Further, the logic circuit produces the resultant inspection signal $S_I$ (see FIG. 2) representing the symbol "o" or "x", in accordance with the numbers shown in both rows (POS) and (NEG). It should be noted that the logic circuit in the circuit 217 is not limited to processing the numbers of the signals $S_{pd}$ and $S_{nd}$. If the logic circuit is constructed to limit the duration of time between the positive and negative decision signals, the logic circuit can then determine whether or not the surface area of the tablet is of a standardized size. Since the appearance detector 204 and the decision circuit 217 (both shown in FIG. 2) are not important in the present invention, detailed explanations will not be further mentioned.

Figure 6A:
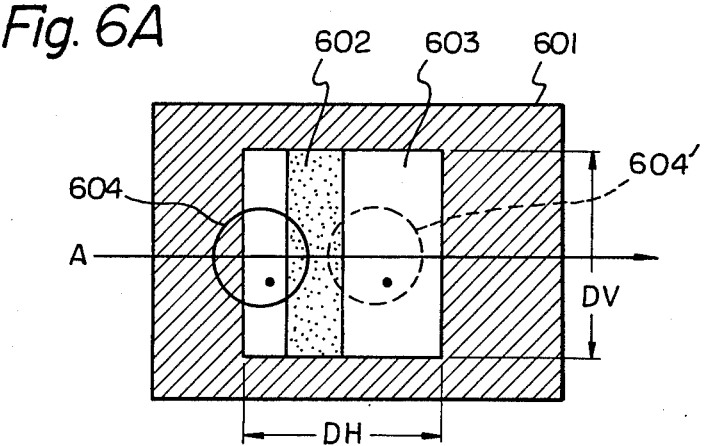
FIGS. 6A and 6B are plan views of a TV image scope, used for explaining the operational principle of the external appearance inspecting system shown in FIG. 2.
Figure 6B:
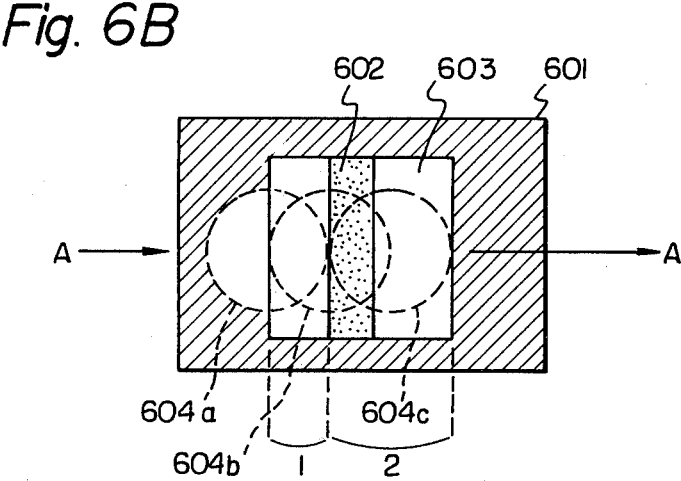

The operational principle of the external appearance inspecting system of FIG. 2 will be explained with reference to FIGS. 6A and 6B. In FIG. 6A, the reference numeral 601 represents the TV image scope. In the scope 601, the detection area 602 (dotted area) and the inspection area 603 (DVxDH) are created. The hatched image area is not used. The reference numeral 604 indicates the image of the tablet having a blot in it, which image is provided in some scanning field. The scanning field is created by great number of horizontal scanning lines being scanned from left to right in the scope 601 and, at the same time, being shifted, sequentially from the top to the bottom of the scope 601. When the image 604 is traversed across the scope 601 in the direction of arrow A (refer to FIG. 2), at first, the image 604 is detected by the detection area 602 (corresponding to the signal $S_d$ in FIG. 2), then the image 604 is inspected by the inspection area 603 (corresponding to the signal $S_i$ in FIG. 2). If the image 604 is detected by the detection area 602 which is created by the $N_{th}$ (N=1, 2, 3 ...) scanning field, then the image 604 is rendered to the inspection area 603 which is created by the $(N+K)_{th}$ (K=1, 2, 3 ...) scanning field. The number K is predetermined, in advance, in the sampling circuit 213. The number K is selected so that the image 604 which is detected by the detection area 602 in the $N_{th}$ scanning field, may be traversed and located entirely within the inspection area 603 during the elapse period of the sequence of K number of the scanning field. Then, the image 604 will be shifted to become a dotted image 604'. Consequently, the inspecting system can always determine the entire external appearance of the tablet with a high degree of accuracy. This is because the system itself detects the appearance of the image 604 and further the system itself undertakes a specified inspection scanning field of the image 604' for starting the operation of the inspection. It is preferable to set the detection area 602 at the position of one third of the horizontal stroke of the inspection area 603 (refer to the proportion 1:2 shown in FIG. 6B). In FIGS. 6B, if the image is detected by the detection area 602 at a dotted image circle (604a), then the image can be inspected, after the aforesaid K number's delay, in the area 603 at a dotted image circle 604b. In this case, the image 604b is entirely arrested within the area 603. If the image is detected by the area 602 at the dotted image circle (604b), then the image can be inspected, after the K number's delay, in the area 603 at a dotted image circle (604c). In this case, the image 604a is also entirely arrested within the area 603. If the image is relatively large in size, the width of the area 602 may be narrow. Contrary to this, if the image is relatively small in size, the width of the area 602 must be wide, for the purpose of complete arresting of the small image. This is because, the entire area 602 is not created in an instant but sequentially from the top to the bottom of the TV image scope 601, in synchronism with the variation of the vertical deflection signal. The entire area 603 is also created sequentially from the top to the bottom of the TV image scope. Further, the TV image scope having such patterns of areas 602 and 603 as shown in FIG. 6B, is effective for introducing only one image at a time to be inspected within the inspection area, in the case where the traversing speed "v" of the image (tablets) in the direction of arrow A, is selected so that the tablet may be traversed one half length thereof during the formation of one scanning field, under the condition where the tablets are arranged with spaces being longer than the length of each tablet. When the transferring speed is selected to be lower than the above mentioned speed "v", only one image will be introduced within the inspection area. However, an inspection with high speed cannot be expected.

Figure 7A:
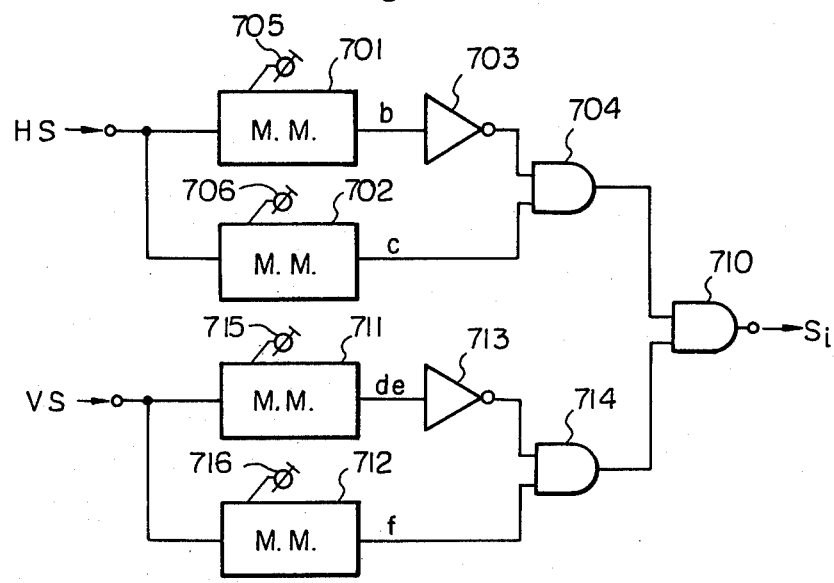
FIG. 7A is a block diagram of an areal mask signal generator 206 shown in FIG. 2.
Figure 7B:
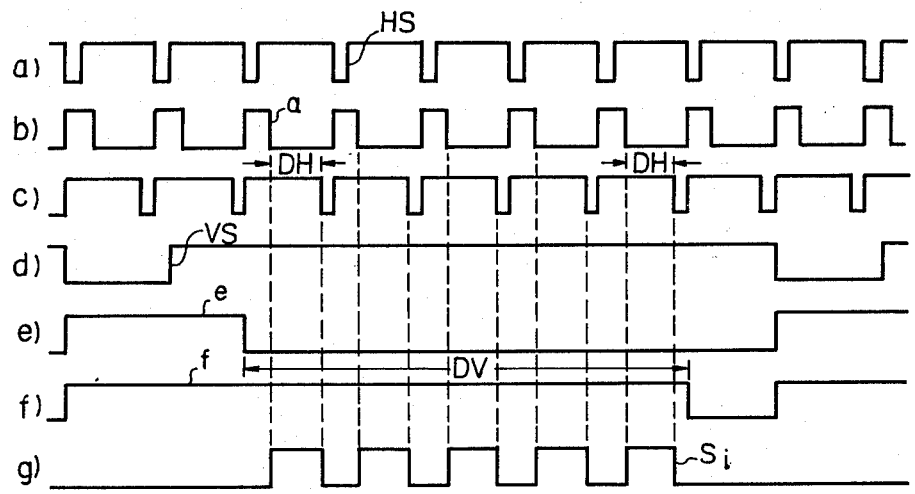
FIG. 7B depicts timing charts used for explaining the circuit shown in FIG. 7A.

Returning to FIG. 2, the areal mask signal generator 206 is comprised of both a first digital circuit for producing the detection area signal $S_d$ and a second digital circuit for producing the inspection area signal $S_i$. Since the first and second digital circuits have identical circuit construction with each other, only the circuit construction of the second digital circuit, that is the areal mask signal generator for generating the inspection area signal $S_i$, is described, as an example, in FIG. 7A. FIG. 7B shows timing charts, used for explaining the generator shown in FIG. 7A. In FIG. 7A, the reference numerals 701, 702, 711 and 712 represent monostable multivibrators (M.M.). The respective time constants can be variable by means of adjusters 705, 706, 715 and 716. The reference numerals 703 and 713 represent inverters. The reference numerals 704, 714 and 710 represent AND gates. The members 701 through 706 are triggered by the horizontal synchronizing signal HS. The members 711 through 716 are triggered by the horizontal synchronizing signal VS. The waveforms of the horizontal and vertical synchronizing signals HS and VS are shown in rows (a) and (d), respectively in FIG. 7B. The adjusters 705 and 706 select the values of said time constants so as to define the horizontal location of the inspection area 603 (see FIGS. 6A and 6B). The adjusters 715 and 716 select the value of said time constants so as to define the vertical location of the area 603. The waveforms of the outputs b, c, e and f from the monostable multivibrators 701, 702, 711 and 712, are, respectively depicted in rows (b), (c), (e) and (f) in FIG. 7B. The durations DH (see row (b)) correspond to the horizontal locations (see DH in FIG. 6A) of the respective scanning lines. The duration DV (see row (e)) corresponds to the vertical location (see DV in FIG. 6A) of the scanning lines. The durations DH and DV are, respectively represented by the outputs from the AND gates 704 and 714. Then, the output of the AND gate 710 becomes the inspection area signal $S_i$ which defines the horizontal and vertical locations of the area 603. Similarly, the detection area signal $S_d$, which defines the horizontal and vertical locations of the detection area 602 (see FIGS. 6A and 6B), can also be produced by an identical digital circuit with the digital circuit shown in FIG. 7A.

Figure 8A:
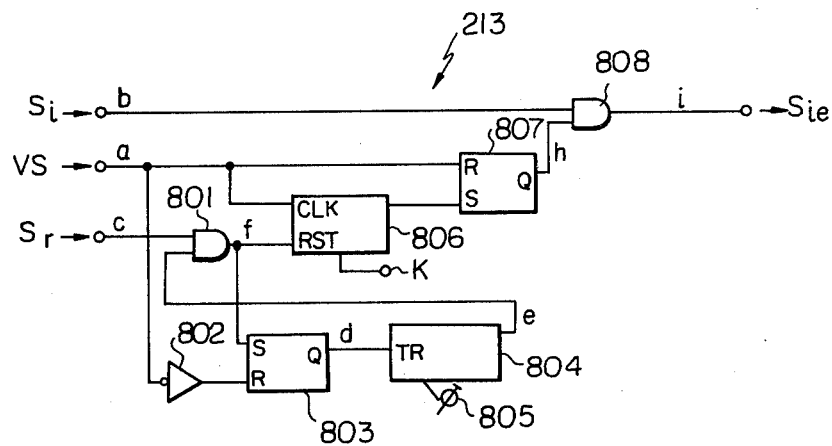
FIG. 8A is a block diagram of a sampling circuit 213 shown in FIG. 2.
Figure 8B:
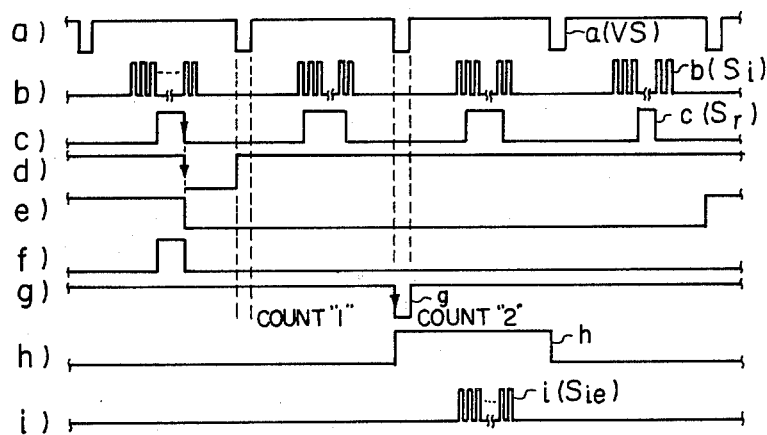
FIG. 8B depicts timing charts, used for explaining the circuit shown in FIG. 8A.

Returning again to FIG. 2, the sampling circuit 213 can be constructed in accordance with, for example, a circuit diagram shown in FIG. 8A. FIG. 8B depicts timing charts, used for explaining the circuit 213 shown in FIG. 8A. In FIGS. 8A and 8B, as previously explained, the circuit 213 receives the inspection area signal $S_i$ of FIG. 2 (refer to row b) in FIG. 8B) and the recognition signal $S_r$ of FIG. 2 (see row c) in FIG. 8B), together with the vertical synchronizing signal VS of FIG. 2 (refer to row a) in FIG. 8B), and produces the effective inspection area signal $S_{ie}$ of FIG. 2 (refer to row i) in FIG. 8B. The output signal $S_{ie}$ determines one specified scanning field according to the aforesaid number K, in order to introduce the image 604' (see FIG. 6A) entirely within the inspection area 603. The number K is a predetermined value. In a case where the number K is predetermined to be "2", this value "2" is preset in a presettable counter 806 (FIG. 8A) via a preset terminal K. In this case, the second counted pulse "g" (see row g) in FIG. 8B) from the counter 806 (see the pulse "g" in FIG. 8A) is effected, and therefore a scanning field signal "h" (see FIG. 8A) becomes effected (see row h) in FIG. 8B). As a result, a signal "i" (see row i) in FIG. 8B) is produced from an AND gate 808 (see the signal "i" in FIG. 8A), as the effective inspection area signal $S_{ie}$. In FIG. 8A, the reference numeral of 801 represents an AND gate, 802 represents an inverter, 803 represents a flip flop, 804 represents a monostable multivibrator, a 805 represents an adjuster for controlling the time constant of the monostable multivibrator 804 and 807 represents a flip flop. Note that the waveforms of the signals "a" through "i" shown in FIG. 8A, are depicted in rows (a) through (i), respectively in FIG. 8B. The presettable counter 806 receives three signals, that is the recognition signal $S_r$ via the AND gate 801, as a reset (RST) signal, the vertical synchronizing signal VS, as a clock (CLK) signal and the preset signal from the reset terminal K. When the counter 806 finishes counting two (K=2) signals VS and, at the same, receives the reset (RST) signal, the counter 806 produces the count completion signal "g". The flip flop 807 receives the signal "g", as a set (S) signal, and produces the scanning field signal "h". The flip flop 807 is reset by the signal VS, if there is no set (S) signal applied thereto. The scanning field signal "h" is used for gating only one signal $S_i$ among the train of the signals $S_i$, as the effective inspection area signal $S_{ie}$.

In the case where the tablets are transfered a very low speed, such a mistake may be created in that two or more successive recognition signals $S_r$ are obtained from the same tablet, although only one signal $S_r$ should be obtained from one tablet. For the purpose of eliminating the above mentioned mistake, the members 802, 803 and 804 are optionally employed in this circuit 213. The flip flop 803 receives both the recognition signal $S_r$, as a set (S) signal, and the vertical synchronizing signal VS via the inverter 802, as a reset (R) signal, and produces an inhibition signal "d" from its $\overline{Q}$ output. The signal "d" triggers, at a trigger input TR, the monostable multivibrator 804. Then the multivibrator 804 produces an inhibition pulse "e" and supplies the pulse "e"

to the AND gate 801 so as to close the gate 801. The pulsewidth of the pulse "e" can be variable by means of the adjuster 805, according to the condition of the transfer speed of the tablets.

As previously mentioned, the external appearance inspecting system itself can detect the appearance of the image of each tablet to be inspected and also the system itself can define a specified inspection scanning field in which each tablet is to be inspected. Therefore, the first one of the previously mentioned two shortcomings of the prior art can be overcome. Further, the system has the following merit. That is, it is possible to create two or more separate pairs of both the detection and inspection areas simultaneously in one TV image scope and, accordingly, it is possible to inspect two or more kinds of tablets which are transferred on the same glass conveyer, but, along respective separate lines.

In the system of FIG. 2, it is preferable to further employ a stroboscope 222 which intermittently illuminates the scope 141 of the TV camera 201, in synchronous with the occurrence of the vertical synchronizing signal VS. A driver 221 energizes the stroboscope 222 in synchronous with the signal VS. The stroboscope 222 flashes in each blanking period of the signal VS. Accordingly, the image of the tablet is strongly projected to the TV camera 201 being comprised of a storage-type camera tube and the image is stored perfectly in the storage mechanism, every time the TV camera scans the tablet to be inspected.

Figure 9A:
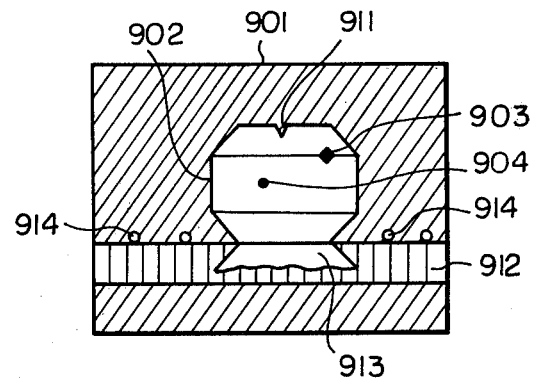
FIGS. 9A and 9B are plan views of a TV image scope, used for explaining a second embodiment of the external appearance inspecting system, according to the present invention.

Now, a second embodiment of the external appearance inspecting system, according to the present invention, will be explained hereinafter. This system is effective for overcoming the second one of the previously mentioned two shortcomings. This second shortcoming will be clarified with reference to FIGS. 9A and 9B. In FIG. 9A, the reference numeral 901 represents a TV image scope. In the scope 901, there are various kinds of images. An image 902 is created by the tablet itself. Images 903 and 904 are created by a small scratch and a blot, both existing on the surface of the tablet. An image 911 is created by a hallmark made on the surface of the tablet. An image 912 is created by the glass conveyer 121 shown in FIG. 1. An image 913 is created by a reflection of light from the conveyor due to the presence of reflective matter on the tablet. Images 914 are created by powder dust on the tablets distributed on the conveyor. The analogue image signals are digitally processed by a conventional Analogue/Digital converter and transformed into digital image signals. The digital image pattern based on the digital image signals is ilustrated in FIG. 9B.

Figure 9B:
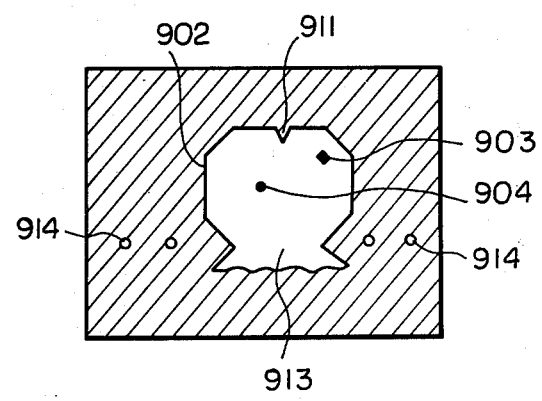
Figure 10:
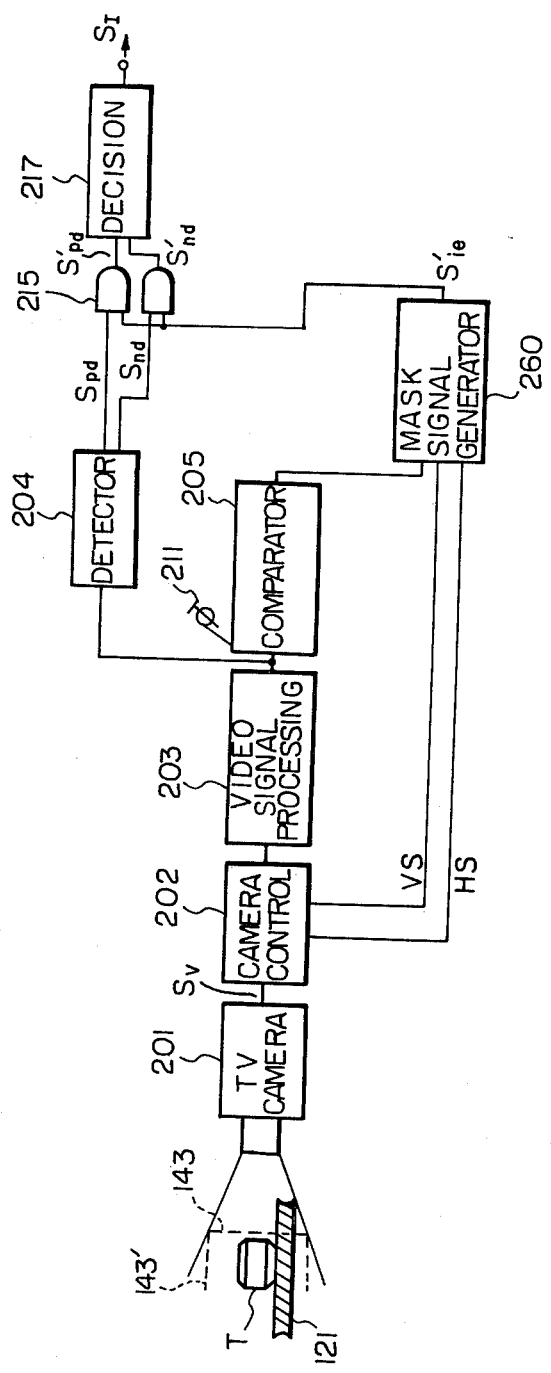
FIG. 10 is a block diagram of a second embodiment of the external appearance inspecting system, according to the present invention.

In FIG. 9B, it should be noted that the images 902, 903 and 904 are images wich require inspection, however, the images 911, 913 and 914 are images which do not require inspection. This is because, the images 911, 913 and 914 are irrelevant to the defects to be inspected. In order to discriminate the images 902, 903 and 904 from the images 911, 913 and 914, an improved inspection area on the inspection area 603 (FIG. 6A), is utilized. FIG. 10 is a block diagram of the second embodiment of the external appearance inspecting system according to the present invention. In FIG. 10, members which are referenced by the same reference numerals and symbols of FIG. 2 are identical members. Accordingly, a block 260 is a newly employed one. This block 260 is the improved areal mask signal generator of the corresponding generator 206 shown in FIG. 2. The TV camera 201 is oriented to the side of the tablet T so as to form the scope 143 and 143' (refer to FIG. 1), thereby the TV image scope 901 of FIG. 9A is obtained. The generator 260 is useful for creating no fixed inspection area, as is the inspection area 603 of FIG. 6A, but creates a variable and floating inspection area in accordance with the variation of the size of the tablet and the positional deviation of the tablet due to, for example, the low frequency vibration of the conveyor. Accordingly, a modified effective inspection signal $S_{ie}'$ is produced from the generator 260 so as to create said variable and floating inspection area.

Figure 11A:
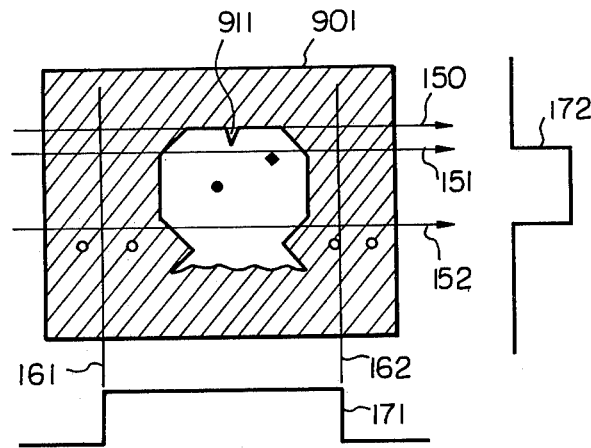
FIG. 11A is a plan view of a TV image scope 901 shown in FIG. 9B, used for explaining a variable and floating inspection area created in the above mentioned system of the second embodiment.
Figure 11B:
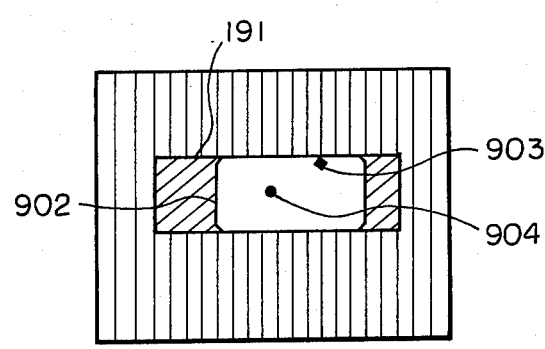
FIG. 11B is a plan view of a TV image scope containing the variable and floating inspection area.

FIG. 11A illustrates a plan view of the TV image scope 901 of FIG. 9B, used for explaining the aforesaid variable and floating inspection area. In FIG. 11A, such an inspection area is defined by horizontal scanning lines 151, 152 and vertical scanning lines 161, 162. The operational principle for defining the lines 151, 152, 161 and 162 is substantially the same as the operational principle mentioned with reference to FIGS. 6A, 7A and 7B. The variable and floating inspection area, defined by the lines 151, 152, 161 and 162, is illustrated in FIG. 11B, as referenced by the reference numeral 191. It should be understood, in FIG. 11B, only the images 902, 903 and 904 are extracted and exposed inside the area 191, which images require inspection. It is important to understand that the first horizontal scanning line 151 of the area 191 starts traversing when a predetermined number of horizontal scanning lines elapsed from the time when a horizontal scanning line 150 initially arrests the image of the top surface of the tablet. That is, the scanning lines from 150 to 151 minus 1 are omitted, because these lines arrest the image of the hallmark 911 which is irrelevant to the inspection of the tablet itself.

Figure 12A:
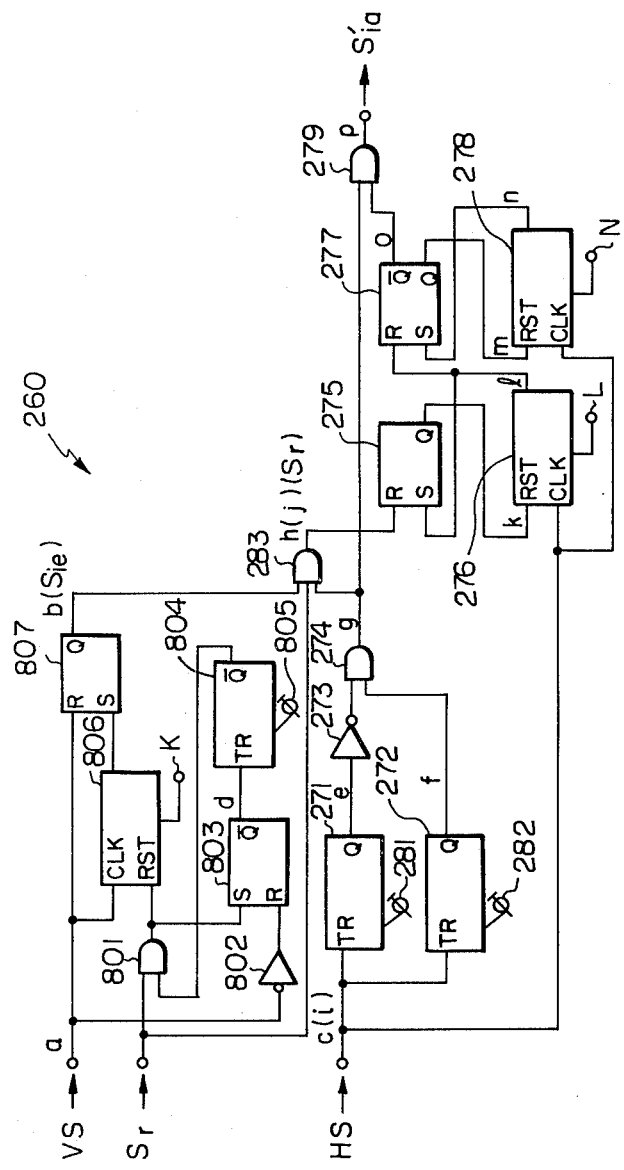
FIG. 12A is a detailed block diagram of an areal mask signal generator 260 shown in FIG. 10.
Figure 12B:
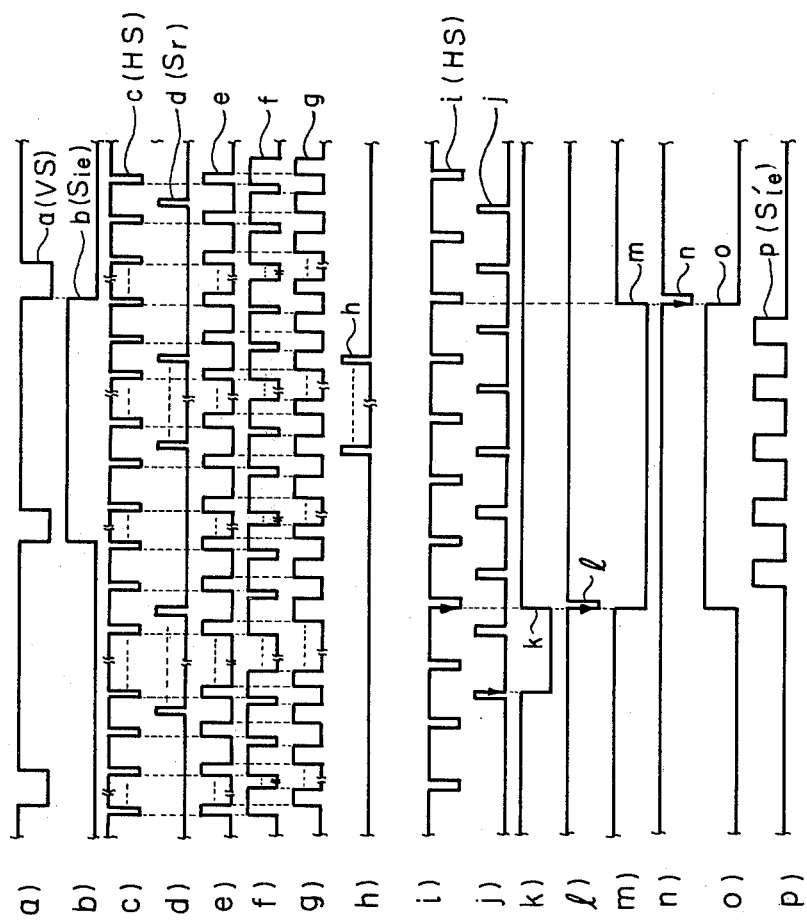
FIG. 12B depicts timing charts, used for explaining the circuit shown in FIG. 12A.

In FIG. 12A, which is a detailed block diagram of the newly employed generator 260 shown in FIG. 10, the meanings of the reference symbols VS, $S_r$, HS and $S_{ie}'$ have already been mentioned with reference to FIG. 10 and FIG. 2. Further, the members 801 through 807 are identical with the respective members having the same numeral. Therefore, the operations of the members 801 through 807 are not mentioned again. The waveforms of the signals a through p of FIG. 12A are, respectively depicted in rows (a) through (p) in FIG. 12B. The monostable multivibrators 271 and 272 receive the horizontal synchronizing signal HS, as respective trigger (TR) pulses, and, respectively produce timing pulses "e" and "f". Then an AND gate 274 receives both the pulse "e" via an inverter 273 and the pulse "f", and produces a timing pulse "g". The timing pulse "g" corresponds to a pulse 171 shown in FIG. 11A and defines the horizontal length of the inspection area 191 (refer to FIG. 11B). The horizontal length of the inspection area 191 can freely be controlled by means of adjusters 281 and 282. The adjusters 281 and 282 control the time constants of the respective monostable multivibrators 271 and 272. The pulse "h" from an AND gate 283 is comprised of the recognition signals $S_r$ which are created within the duration of the effective inspection area signal $S_{ie}$ (b), and the signals $S_{ie}$ and $S_r$ are gated by the signal "g". The pulse "h" is applied to a flip flop 275, as a reset (R) signal thereof. The output "k" of the flip flop 275 is applied to a presettable counter 276, as a reset (RST) signal. Then the counter 276 starts counting the number of the horizontal synchronizing signals HS, as clock (CLK) pulses. A preset value is supplied, in advance, to the counter 276 through a preset terminal L. The preset value from the terminal L defines the vertical length from the line 150 to the line 151 (see FIG.

11A), for the purpose of eliminating the image which is irrelevant to the inspection. The count completion pulse "l" is applied, on one hand, to the flip flop 275, as a set (S) signal. Then the counter 276 is reset by the Q output from the flip flop 275, and thereby the counter 276 stops counting the signal HS. The count completion pulse "l" is applied, on the other hand, to a flip flop 277, as a reset (R) signal. Then the Q output "m" from the flip flop 277 is applied to a presettable counter 278, as a reset (RST) signal. Therefore, the counter 278 starts counting the number of the horizontal synchronizing signals HS, as clock (CLK) pulses. A preset value is supplied, in advance, to the counter 278 through a preset terminal N. The preset value from the terminal N defines the vertical length from the line 151 to the line 152 (see FIG. 11A), for the purpose of extracting the area to be inspected. A count completion pulse "n" sets the flip flop 277 and the Q output "m" thereof resets the counter 278, and thereby the counter 278 stops counting the signal HS. The $\overline{Q}$ output "O" (corresponding to a pulse 172 shown in FIG. 11A) of the flip flop 277 is applied to an AND gate 279 for gating the aforesaid timing pulses "g". As a result, an output "p" from the AND gate 279 is provided, as the modified effective inspection area signal $S_{ie}'$.

FIG. 13 is a plan view of the TV image scope, used for explaining the operation of the system shown in FIG. 10. FIGS. 14A through 14F depict timing charts, wherein columns (a) through (d) represent four different modes which, respectively correspond to scanning modes (a) through (d) shown in FIG. 13. FIG. 14A depicts the waveforms of the horizontal synchronizing signal HS. FIG. 14B depicts the waveforms of the video signal $S_v$, as in FIG. 5A. FIG. 14C depicts the waveforms of the positive and negative decision signals $S_{pd}$ and $S_{nd}$, together with the positive and negative threshold levels $T_p$ and $T_n$, as in FIG. 5B. The signals $S_{pd}$ and $S_{nd}$ are transformed to square pulse signals $S_{pd}'$ and $S_{nd}'$ as shown in FIG. 14D, by means of a conventional waveshaper. FIG. 14E depicts the waveform of the effective inspection area signal $S_{ie}'$. The signals $S_{pd}'$ and $S_{nd}'$ of FIG. 14D, which are produced within the duration of the signal $S_{ie}'$, become final and effective inspection area signals which are depicted in FIG. 14F, as the signals $S_{pde}$ and $S_{nde}$. It should be recognized that the signals $S_{pde}$ and $S_{nde}$ are the decision signals obtained only from the variable and floating inspection area 191. The final decision circuit 217 produces the resultant inspection signal $S_I$ based on the logic patterns of the signals $S_{pde}$ and $S_{nde}$. That is, the circuit 217 decides that the image in mode (b) includes no defect, but, the image in mode (c) includes a defect.

What is claimed is:

1. An external appearance inspecting system comprising:
    a TV camera for forming a TV image scope oriented to a flow of objects to be inspected on a conveyor;
    a camera control unit for producing a video signal of the TV image scope;
    a video signal processing circuit for processing the video signal;
    an appearance detector which receives the processed video signal and extracts portions indicating visible features of the object from the processed video signal;
    a decision circuit for discriminating whether or not the extracted video signal is created by defects contained in the object;
    a level comparator for differentiating a video signal indicating the image of the object from a video signal indicating the image of the background;
    an areal mask signal generator which produces both a first area signal and a second area signal, based on horizontal and vertical synchronizing signals and the output from the level comparator, the first area signal defining a detection area and the second area signal defining an inspection area, and the generator further determines a $(N+K)_{th}$ ($N=1, 2, 3 \ldots,$ $K=1, 2, 3 \ldots$) scanning field of the inspection area, in case the image of the object was detected in the detection area at a $N_{th}$ scanning field, the $(N+K)_{th}$ scanning field being adapted to inspect the image of the object entirely, and;
    an AND gate means which receives both a signal indicating the $(N+K)_{th}$ scanning field and an output from the appearance detector and produces an output therefrom to be supplied to the decision circuit.

2. A system as set forth in claim 1, wherein the video signal processing circuit is comprised of both a low pass filter means and an amplifying means.

3. A system as set forth in claim 1, wherein the appearance detector is comprised of both a differentiating means and a level comparator means connected thereto in series.

4. A system as set forth in claim 1, wherein the areal mask signal generator includes: a first presettable counter to which a predetermined value indicating the number K is preset; monostable multivibrators which are triggered by the output from the level comparator and which define scanning lines for creating the inspection area, and; a second presettable counter to which a predetermined value is preset, which predetermined value further specifies only an effective area, for the inspection, in the inspection area.

5. An external appearance inspecting system comprising:
    a TV camera for forming a TV image scope oriented to a flow of objects to be inspected on a conveyer;
    a camera control unit for producing a video signal of the TV image scope;
    a video signal processing circuit for processing the video signal, an appearance detector which receives the processed video signal and extracts portions indicating visible features of the object from the processed video signal;
    a decision circuit for discriminating whether or not the extracted video signal is created by defects contained in the object;
    a level comparator for differentiating a video signal indicating the image of the object from a video signal indicating the image of the background;
    an areal mask signal generator which produces both a first area signal and a second area signal, based on horizontal and vertical synchronizing signals and creates the first area signal defining a detection area and the second area signal defining an inspection area;
    a sampling circuit for sampling a $(N+K)_{th}$ ($N=1, 2, 3 \ldots, K=1, 2, 3 \ldots$) scanning field of the inspection area, in case the image of the object was detected in the detection area at a $N_{th}$ scanning field, the $(N+K)_{th}$ scanning field being adapted to inspect the image of the object entirely based on the first and second area signals from the areal mask signal generator and the output from the level comparator, and;

an AND gate means which receives both a signal indicating the $(N+K)_{th}$ scanning field and an output from the appearance detector and produces an output therefrom to be supplied to the decision circuit.

6. A system as set forth in claim 1, wherein the video signal processing circuit is comprised of both a low pass filter means and an amplifying means.

7. A system as set forth in claim 5, wherein the appearance detector is comprised of both a differentiating means and a level comparator means connected thereto in series.

8. A system as set forth in claim 5, wherein the areal mask signal generator includes monostable multivibrators which are triggered by the horizontal and vertical synchronizing signals and which define the inspection area.

9. A system as set forth in claim 5, wherein the sampling circuit includes a presettable counter to which a predetermined value indicating the number K is preset.

* * * * *